United States Patent
Reustle et al.

(10) Patent No.: US 12,201,451 B2
(45) Date of Patent: Jan. 21, 2025

(54) OPTICAL SHUNT REDUCTION USING OPTICALLY ABSORPTIVE MATERIALS IN A MEDICAL SENSOR

(71) Applicant: Covidien LP, Mansfield, MA (US)

(72) Inventors: Linden A. Reustle, Milliken, CO (US); Jacob D. Dove, Lafayette, CO (US); Sarah L. Hayman, Boulder, CO (US); Derek L. Moody, Longmont, CO (US); Shai Fleischer, Modiin (IL)

(73) Assignee: COVIDIEN LP, Mansfield, MA (US)

( * ) Notice: Subject to any disclaimer, the term of this patent is extended or adjusted under 35 U.S.C. 154(b) by 609 days.

(21) Appl. No.: 17/085,094

(22) Filed: Oct. 30, 2020

(65) Prior Publication Data

US 2022/0133233 A1    May 5, 2022

(51) Int. Cl.
    *A61B 5/00*    (2006.01)
(52) U.S. Cl.
    CPC .......... *A61B 5/6833* (2013.01); *A61B 5/0002* (2013.01); *A61B 5/0059* (2013.01); *A61B 2562/12* (2013.01); *A61B 2562/164* (2013.01); *A61B 2562/185* (2013.01)
(58) Field of Classification Search
    CPC ... A61B 5/6833; A61B 5/0002; A61B 5/0059; A61B 2562/12; A61B 2562/164; A61B 2562/185; A61B 5/14552; A61B 5/0075; A61B 5/02427
    See application file for complete search history.

(56) References Cited

U.S. PATENT DOCUMENTS

| | | | | |
|---|---|---|---|---|
| 5,246,003 A * | 9/1993 | DeLonzor | .......... | A61B 5/02427 600/344 |
| 5,752,914 A * | 5/1998 | Delonzor | .......... | H05K 9/00 442/131 |
| 7,341,559 B2 * | 3/2008 | Schulz | .......... | A61B 5/14552 600/500 |
| 7,563,110 B2 * | 7/2009 | Al-Ali | .......... | A61B 5/0205 439/77 |
| 7,869,849 B2 | 1/2011 | Ollerdessen et al. | | |
| 7,880,884 B2 | 2/2011 | Medina | | |
| 7,899,510 B2 | 3/2011 | Hoarau | | |
| 7,904,130 B2 | 3/2011 | Raridan, Jr. | | |
| 8,000,760 B2 | 8/2011 | Mannheimer et al. | | |
| 8,229,533 B2 * | 7/2012 | Diab | .......... | A61B 5/6829 600/323 |

(Continued)

OTHER PUBLICATIONS

International Search Report and Written Opinion; International Application No. PCT/US2021/057012; International Filing Date Oct. 28, 2021; Date of Mailing Feb. 16, 2022; 11 pages.

*Primary Examiner* — Pascal M Bui Pho
*Assistant Examiner* — Taylor Deutsch
(74) *Attorney, Agent, or Firm* — Fletcher Yoder, P.C.

(57) ABSTRACT

A patient monitoring sensor having a communication interface, through which the patient monitoring sensor can communicate with a monitor is provided. The patient monitoring sensor includes a light-emitting diode (LED) communicatively coupled to the communication interface and a detector, communicatively coupled to the communication interface, capable of detecting light. The patient monitoring sensor includes an optically absorptive material at least partially between the LED and the detector to reduce or prevent shunting of light to the detector.

20 Claims, 3 Drawing Sheets

(56) References Cited

U.S. PATENT DOCUMENTS

| | | |
|---|---|---|
| 8,265,724 B2 | 9/2012 | Petersen |
| 8,600,469 B2 | 12/2013 | Raridan |
| 8,923,944 B2 | 12/2014 | Petersen |
| 9,610,040 B2* | 4/2017 | Besko ................ A61B 5/02427 |
| 9,642,576 B2 | 5/2017 | Petersen |
| 2002/0165440 A1* | 11/2002 | Mason .................. H05K 1/189 |
| | | 29/846 |
| 2004/0054291 A1* | 3/2004 | Schulz ................ A61B 5/6816 |
| | | 600/500 |
| 2004/0267104 A1* | 12/2004 | Hannula .............. A61B 5/6804 |
| | | 600/340 |
| 2008/0076982 A1 | 3/2008 | Ollerdessen et al. |
| 2010/0249554 A1 | 9/2010 | McKenna et al. |
| 2013/0158372 A1* | 6/2013 | Haisley ............... A61B 5/1455 |
| | | 600/310 |

* cited by examiner

OPTICAL SHUNT REDUCTION USING OPTICALLY ABSORPTIVE MATERIALS IN A MEDICAL SENSOR

FIELD

The present disclosure relates generally to light-detecting medical devices, and more particularly, to medical devices that monitor physiological parameters of a patient utilizing a light source and a photodetector, such as pulse oximeters.

BACKGROUND

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient uses attenuation of light to determine physiological characteristics of a patient. This is used in pulse oximetry, and the devices built based upon pulse oximetry techniques. Light attenuation is also used for regional or cerebral oximetry. Oximetry may be used to measure various blood characteristics, such as the oxygen saturation of hemoglobin in blood or tissue, the volume of individual blood pulsations supplying the tissue, and/or the rate of blood pulsations corresponding to each heartbeat of a patient. The signals can lead to further physiological measurements, such as respiration rate, glucose levels or blood pressure.

One issue in such sensors relates to light shunting, which is light that passes, not though skin tissue, but rather through a pulse oximetry bandage between light emitting diodes (LEDs) and photodetectors in pulse oximetry sensors. Such shunted light can pass through various paths in the sensor that is not through tissue, for example through the center of the bandage between an LED and a photodetector. Shunting is a problem because it adds error to an oximetry calculation due to light hitting the photodetector that has not passed through such patient tissue, as expected.

Accordingly, light-detecting sensors, including light-detecting medical sensors avoiding such problems are needed in the art.

SUMMARY

The techniques of this disclosure generally relate to light-detecting sensors, including light-detecting medical devices that monitor physiological parameters of a patient, such as pulse oximeters.

In one aspect, the present disclosure provides a patient monitoring sensor having a communication interface, through which the patient monitoring sensor can communicate with a monitor. The patient monitoring sensor also includes a light-emitting source, for example a light-emitting diode (LED), communicatively coupled to the communication interface and a detector capable of detecting light. In exemplary embodiments, to prevent or reduce shunting of light, an optically absorptive material is provided at least partially between an LED and photodetector of the sensor.

In exemplary aspects, the optically absorptive material includes an optically absorptive black material, provided at least partially between an LED and photodetector of the sensor, for example as a flat black material provided as an electromagnetic shielding film on the photodetector lines of a flex circuit for a sensor.

In another aspect, the optically absorptive material includes a flat black material integrated into a sensor bandage at least partially between the LED and photodetector, for example in such a way that it wraps the optical components of the sensor (to lesser or greater degrees).

In another aspect, the disclosure provides a patient monitoring system, having a patient monitor coupled to a patient monitoring pulse oximetry sensor. The patient monitoring pulse oximetry sensor includes a communication interface, through which the patient monitoring sensor can communicate with the patient monitor. The patient monitoring sensor also includes a light-emitting diode (LED) communicatively coupled to the communication interface and a detector capable of detecting light. The patient monitoring sensor further includes an optically absorptive material is provided at least partially between an LED and photodetector of the pulse oximetry sensor, as described in exemplary embodiments.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

The present disclosure recognizes the problems associated with light shunting in patient monitoring sensors utilizing LED(s) and photodetector(s), including reductions in accuracy of the sensor and increased error due to unwanted light paths being detected by the photodetector(s), as has been described above.

Accordingly, the present disclosure describes a patient monitoring sensor that includes an optically absorptive material is provided at least partially between an LED and photodetector of the sensor.

In exemplary aspects, the optically absorptive material includes an optically absorptive black material, provided at least partially between an LED and photodetector of the sensor. Such a material absorbs photons that pass through the sensor bandage or otherwise between optical components, as in an optical shunt, advantageously increasing accuracy of the sensor and reducing error due to unwanted light paths being detected by the photodetector.

In another aspect, the optically absorptive material includes a flat black material provided as an electromagnetic shielding film on a flex circuit at least partially between an LED and photodetector of the sensor. Another aspect provides the optically absorptive material as a flat black electromagnetic shielding film on the flex circuit between any LEDs and photodetectors on the sensor. In exemplary embodiments, such electromagnetic shielding film is provided on the photodetector lines of a flex circuit for a sensor.

In another aspect, the optically absorptive material includes a flat black material integrated into a sensor bandage at least partially between the LED and photodetector. Another aspect provides the optically absorptive material as a flat black material integrated into the bandage in such a way that it at wraps the optical components of the sensor (to lesser or greater degrees).

In another aspect, the disclosure provides a patient monitoring system, having a patient monitor coupled to a patient monitoring sensor. The patient monitoring sensor includes a communication interface, through which the patient monitoring sensor can communicate with the patient monitor. The patient monitoring sensor also includes a light-emitting diode (LED) communicatively coupled to the communication interface and a detector, capable of detecting light. The patient monitoring sensor further includes an optically absorptive material is provided at least partially between an LED and photodetector of the sensor, as described in exemplary embodiments above.

Figure 1:
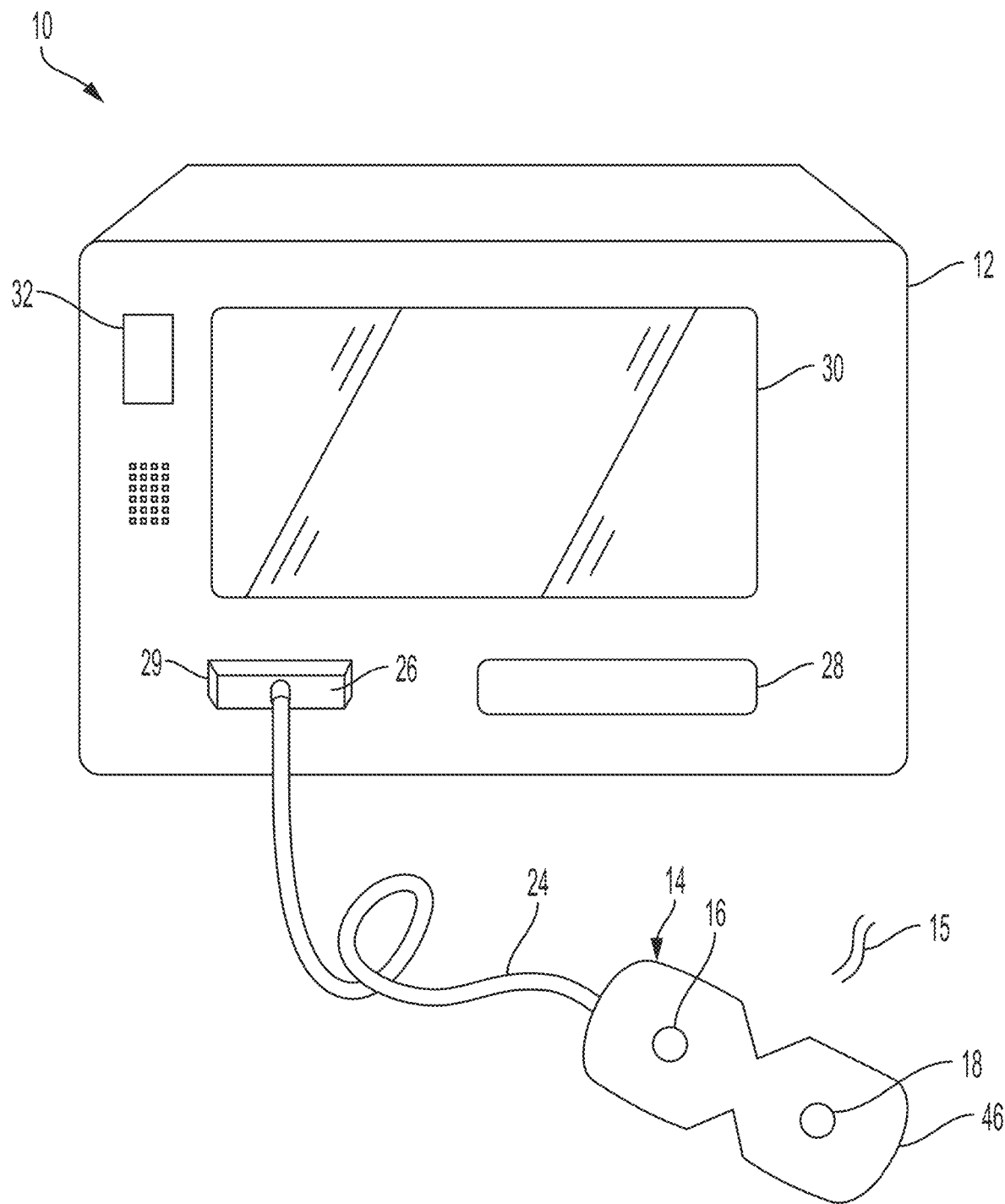
FIG. 1 illustrates a perspective view of an exemplary patient monitoring system including a patient monitor and a patient monitoring sensor, in accordance with an embodiment.

Referring now to FIG. 1, an embodiment of a patient monitoring system 10 that includes a patient monitor 12 and a sensor 14, such as a pulse oximetry sensor, to monitor physiological parameters of a patient is shown. By way of example, the sensor 14 may be a NELLCOR™, or INVOS™ sensor available from Medtronic (Boulder, CO), or another type of oximetry sensor. Although the depicted embodiments relate to sensors for use on a patient's fingertip, toe, or earlobe, it should be understood that, in certain embodiments, the features of the sensor 14 as provided herein may be incorporated into sensors for use on other tissue locations, such as the forehead and/or temple, the heel, stomach, chest, back, or any other appropriate measurement site. Additionally, although the depicted embodiments relate to pulse oximetry sensors, it should be understood that the features described in the present disclosure also relate to any sensor utilizing one or more light sources and one or more photodetectors.

In the embodiment of FIG. 1, the sensor 14 is a pulse oximetry sensor that includes one or more emitters 16 and one or more detectors 18. For pulse oximetry applications, the emitter 16 transmits at least two wavelengths of light (e.g., red and/or infrared (IR)) into a tissue of the patient. For other applications, the emitter 16 may transmit 3, 4, or 5 or more wavelengths of light into the tissue of a patient. The detector 18 is a photodetector selected to receive light in the range of wavelengths emitted from the emitter 16, after the light has passed through the tissue. Additionally, the emitter 16 and the detector 18 may operate in various modes (e.g., reflectance or transmission). In certain embodiments, the sensor 14 includes sensing components in addition to, or instead of, the emitter 16 and the detector 18. For example, in one embodiment, the sensor 14 may include one or more actively powered electrodes (e.g., four electrodes) to obtain an electroencephalography signal.

The sensor 14 also includes a sensor body 46 to house or carry the components of the sensor 14. In exemplary embodiments, the body 46 includes a backing, or liner, provided around the emitter 16 and the detector 18, as well as an adhesive layer (not shown) on the patient side. The sensor 14 may be reusable (such as a durable plastic clip sensor), disposable (such as an adhesive sensor including a bandage/liner materials), or partially reusable and partially disposable.

In the embodiment shown, the sensor 14 is communicatively coupled to the patient monitor 12. In certain embodiments, the sensor 14 may include a wireless module configured to establish a wireless communication 15 with the patient monitor 12 using any suitable wireless standard. For example, the sensor 14 may include a transceiver that enables wireless signals to be transmitted to and received from an external device (e.g., the patient monitor 12, a charging device, etc.). The transceiver may establish wireless communication 15 with a transceiver of the patient monitor 12 using any suitable protocol. For example, the transceiver may be configured to transmit signals using one or more of the ZigBee® standard, 802.15.4x standards, WirelessHART® standard, Bluetooth® standard, IEEE 802.11x standards, or MiWi™ standard. Additionally, the transceiver may transmit a raw digitized detector signal, a processed digitized detector signal, and/or a calculated physiological parameter, as well as any data that may be stored in the sensor, such as data relating to wavelengths of the emitters 16, or data relating to input specification for the emitters 16, as discussed below. Additionally, or alternatively, the emitters 16 and detectors 18 of the sensor 14 may be coupled to the patient monitor 12 via a cable 24 through a plug 26 (e.g., a connector having one or more conductors) coupled to a sensor port 29 of the monitor. In certain embodiments, the sensor 14 is configured to operate in both a wireless mode and a wired mode. Accordingly, in certain embodiments, the cable 24 is removably attached to the sensor 14 such that the sensor 14 can be detached from the cable to increase the patient's range of motion while wearing the sensor 14.

The patient monitor 12 is configured to calculate physiological parameters of the patient relating to the physiological signal received from the sensor 14. For example, the patient monitor 12 may include a processor configured to calculate the patient's arterial blood oxygen saturation, tissue oxygen saturation, pulse rate, respiration rate, blood pressure, blood pressure characteristic measure, autoregulation status, brain activity, and/or any other suitable physiological characteristics. Additionally, the patient monitor 12 may include a monitor display 30 configured to display information regarding the physiological parameters, information about the system (e.g., instructions for disinfecting and/or charging the sensor 14), and/or alarm indications. The patient monitor 12 may include various input components 32, such as knobs, switches, keys and keypads, buttons, etc., to provide for operation and configuration of the patient monitor 12. The patient monitor 12 may also display information related to alarms, monitor settings, and/or signal quality via one or more indicator lights and/or one or more speakers or audible indicators. The patient monitor 12 may also include an upgrade slot 28, in which additional modules can be inserted so that the patient monitor 12 can measure and display additional physiological parameters.

Because the sensor 14 may be configured to operate in a wireless mode and, in certain embodiments, may not receive power from the patient monitor 12 while operating in the wireless mode, the sensor 14 may include a battery to provide power to the components of the sensor 14 (e.g., the emitter 16 and the detector 18). In certain embodiments, the battery may be a rechargeable battery such as, for example, a lithium ion, lithium polymer, nickel-metal hydride, or nickel-cadmium battery. However, any suitable power source may be utilized, such as, one or more capacitors and/or an energy harvesting power supply (e.g., a motion generated energy harvesting device, thermoelectric generated energy harvesting device, or similar devices).

As noted above, in an embodiment, the patient monitor 12 is a pulse oximetry monitor and the sensor 14 is a pulse oximetry sensor. The sensor 14 may be placed at a site on a patient with pulsatile arterial flow, typically a fingertip, toe, forehead or earlobe, or in the case of a neonate, across a foot. Additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, and around or in front of the ear. The patient monitoring system 10 may include sensors 14 at multiple locations. The emitter 16 emits light which passes through the blood perfused tissue, and the detector 18 photoelectrically senses the amount of light reflected or transmitted by the tissue. The patient monitoring system 10 measures the intensity of light that is received at the detector 18 as a function of time.

A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The amount of light detected or absorbed may then be used to calculate any of a number of physiological parameters, including oxygen saturation (the saturation of oxygen in pulsatile blood, SpO2), an amount of a blood constituent (e.g., oxyhemoglobin), as well as a physiological rate (e.g., pulse rate or respiration rate) and when each individual pulse or breath occurs. For SpO2, red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood, such as from empirical data that may be indexed by values of a ratio, a lookup table, and/or from curve fitting and/or other interpolative techniques.

Figure 2:
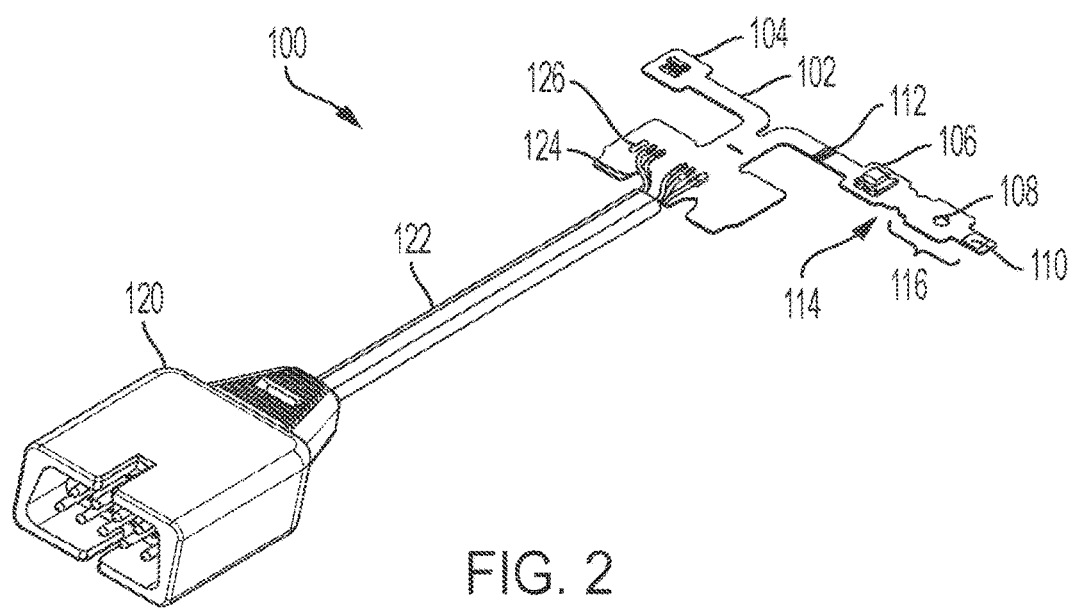
FIG. 2 illustrates a perspective view of an exemplary patient monitoring sensor, in accordance with an embodiment.

Referring now to FIG. 2, an embodiment of a patient monitoring sensor 100 in accordance with an embodiment is shown. As may be seen, the shape or profile of various components may vary. The sensor 100 includes a body 102 that includes a flexible circuit. The sensor 100 includes an LED 104 (for example, a surface mount LED) and a detector 106 disposed on the body 102 of the sensor 100.

While any number of exemplary sensor designs are contemplated herein, in the illustrated exemplary embodiment, the body 102 includes a flap portion 116 that includes an aperture 108. The flap portion 116 is configured to be folded at a hinge portion 114 such that the aperture 108 overlaps the detector 106 to allow light to pass through. In one embodiment, the flap portion 116 includes an adhesive 110 that is used to secure the flap portion 116 to the body 102 after the flap portion 116 is folded at the hinge portion 114.

The sensor 100 includes a plug 120 that is configured to be connected to a patient monitoring system, such as the one shown in FIG. 1. The sensor 100 also includes a cable 122 that connects the plug 120 to the body 102 of the sensor 100. The cable 122 includes a plurality of wires 124 that connect various parts of the plug 120 to terminals 126 disposed on the body 102. The flexible circuit is disposed in the body 102 and connects the terminals 126 to the LED 104 and the detector 106. In addition, one of the terminals 126 connect a ground wire to the flexible circuit.

In exemplary embodiments, the aperture 108 is configured to provide electrical shielding to the detector 106. In exemplary embodiments, aperture 108 also limits the amount of light that is received by the detector 106 to prevent saturation of the detector. In exemplary embodiments, the configuration of the aperture 108, i.e., a number, shape, and size of the openings that define the aperture 108 can vary. As illustrated, in one embodiment, the aperture 108 includes a single round opening. In other embodiments, the aperture 108 can include one or more openings that have various shapes and sizes. The configuration of the aperture 108 is selected to provide electrical shielding for the detector 106 and/or control the amount of light that is received by the detector 106. In exemplary embodiments, the body 102 includes a visual indicator 112 that is used to assure proper alignment of the flap portion 116 when folded at the hinge portion 114. Further, the shape of the material of the flap portion 116 around the aperture 108 can vary, while at the same time increasing the surface area around the detector to reduce the contact pressure from the detector on the skin.

Figure 3:
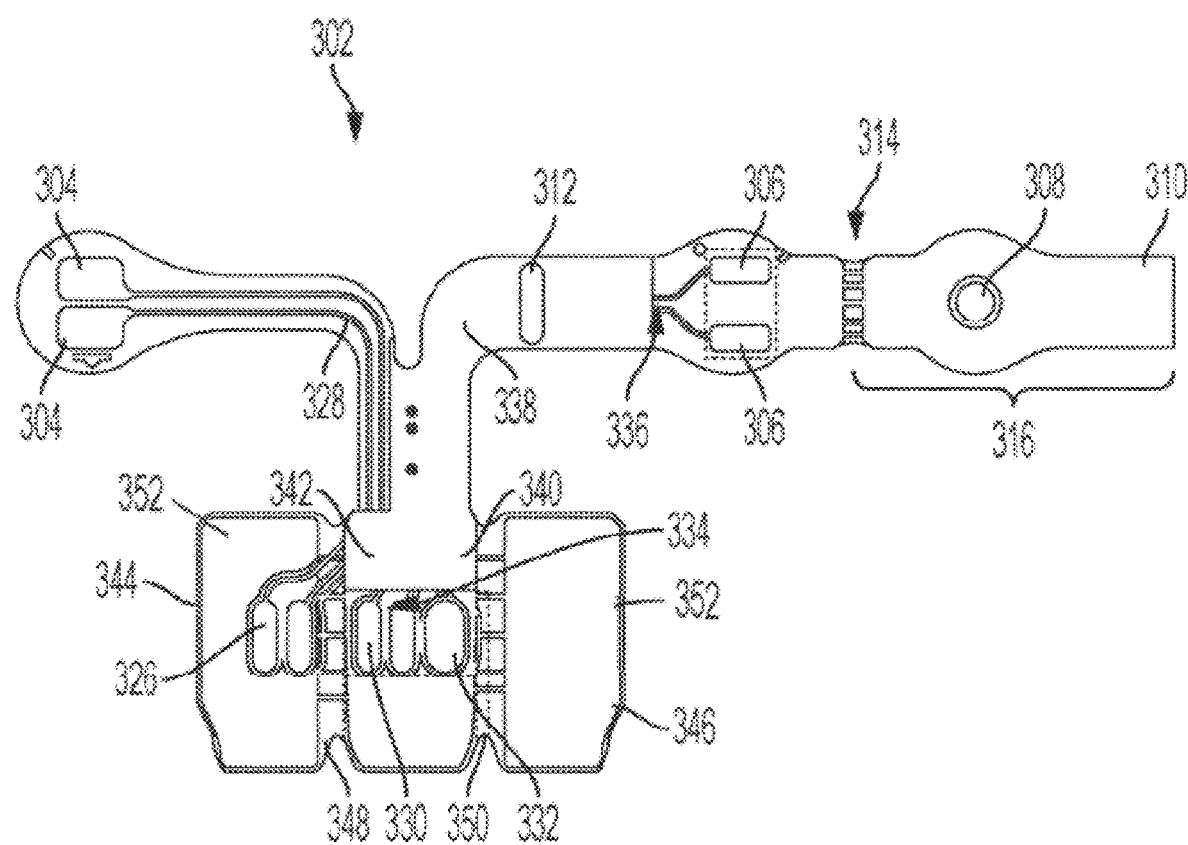
FIG. 3 illustrates a schematic view of a portion of an exemplary patient monitoring sensor incorporating an optically absorptive material, in accordance with an embodiment.

FIG. 3 illustrates an embodiment of a patient monitoring sensor with a body 302 that includes a flexible circuit. The sensor includes LED location(s) 304, with related traces and detector location(s) 306 and related traces disposed on the body 302 of the sensor.

Figure 4:
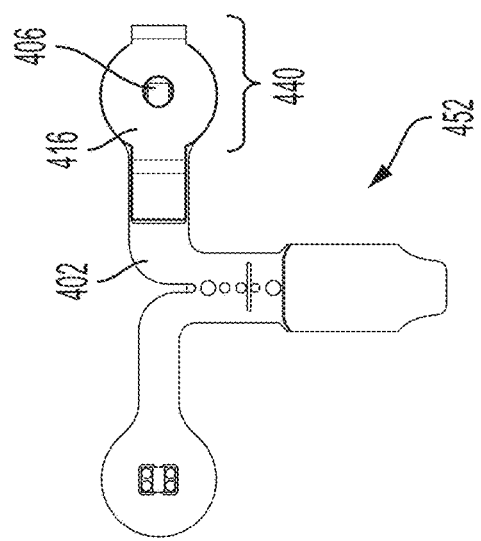
FIG. 4 illustrates top elevation view of a portion of an exemplary patient monitoring sensor, in accordance with an embodiment.

In the illustrated exemplary embodiment, the body 302 includes a flap portion 316 that includes an aperture 308. The flap portion 316 is configured to be folded at a hinge portion 314 such that the aperture 308 overlaps the detector (at 306) to allow light to pass through. In one embodiment, the flap portion 316 includes an adhesive 310 that is used to secure the flap portion 316 to the body 302 after the flap portion 316 is folded at the hinge portion 314. In exemplary embodiments, the body 302 includes a visual indicator 312 that is used to assure proper alignment of the flap portion 316 when folded at the hinge portion 314 during assembly or manufacture. Referring further to FIG. 4, faraday cage 440 is illustrated as formed around the detector 406 by folding the flap portion 416 over a portion of the body 402 of the sensor.

With further regard to the exemplary flexible circuit illustrated at FIG. 3, terminals 326 are provided to connect to the LED (at 304), for example via conductive paths 328. Additionally, terminals 330 are provided to connect to detector 306 and terminal 332 connects a ground wire to the flexible circuit.

In the illustrated exemplary embodiment, conductive paths for the detector are covered by an optically absorptive material including a flat black material 338 provided as an electromagnetic shielding film on a flex circuit at least partially between an LED (at 304) and photodetector (at 306) of the sensor. As is illustrated in FIG. 3, such electromagnetic shielding film is provided over the photodetector lines, which (by virtue of being covered by the electromagnetic shielding film) are only shown at detector terminal 330 connection points, shown generally at 334, and at detector (at 306) connection points, shown generally at 336. In the illustrated exemplary embodiment of FIG. 3, portions of the ground connector are also covered by the electromagnetic shielding film at 340, as are at least portions of the LED conductive traces, shown generally at 342.

In exemplary embodiments, such electromagnetic shielding films are selected based upon a thickness and flexibility so as to not interfere with patient comfort. Exemplary overall thicknesses include micrometer sizes up to about 100 micrometers, up to about 75 micrometers, up to about 50 micrometers, up to about 25 micrometers, etc., or less.

An exemplary electromagnetic shielding film include a metallic deposition layer, an anisotropic conductive adhesive layer and one or more insulation layers. One exemplary electromagnetic shielding film material is a portion of SF-PC5000 film from Tatsuta, with outer transparent layers removed. With regard to the modified SF-PC5000 material, the thickness of is approximately 21-22 micrometers after removal of such transparent layers.

Flex circuit flaps 344 and 346 further fold over fold lines 348 and 350 to provide a folded configuration, similar to that of FIG. 4, shown generally at 452. In exemplary embodiments, folding of flaps that also include electromagnetic shielding film, shown generally at 352, provides shielding around plural sides (e.g., 360 degree shielding) for traces/wires.

While detector and LED wires are shielded by the cable itself, once the cable jacket and shield are stripped back where the wires are soldered, shielding from the cable is removed. Accordingly, shielding provided on the flaps can be a particularly effective structure and method with regard to detector wires, while at the same time providing a smaller form factor/size for the sensor itself.

In exemplary embodiments, an unfolded configuration in line with embodiments such as FIG. 3 allows all wires to be soldered or otherwise connected on a single side (e.g., the top side), providing benefit to manufacture ease and cost of the sensor. Flap 346 folds counter-clockwise on top to provide shielding to top side of detector wires. Flap 344 also folds counter-clockwise underneath the electromagnetic shielding film at 340, which provides 2 layers of shielding, which is the electromagnetic shielding film of the flex circuit, between the detector and LED wires and provides an additional layer of separation between LED and detector wires, further minimizing electrical cross-talk between those component aspects. Such construction also allows use of the various sides without addition of difficulty to manufacturing to make a smaller (and shielded) component.

Figure 5:
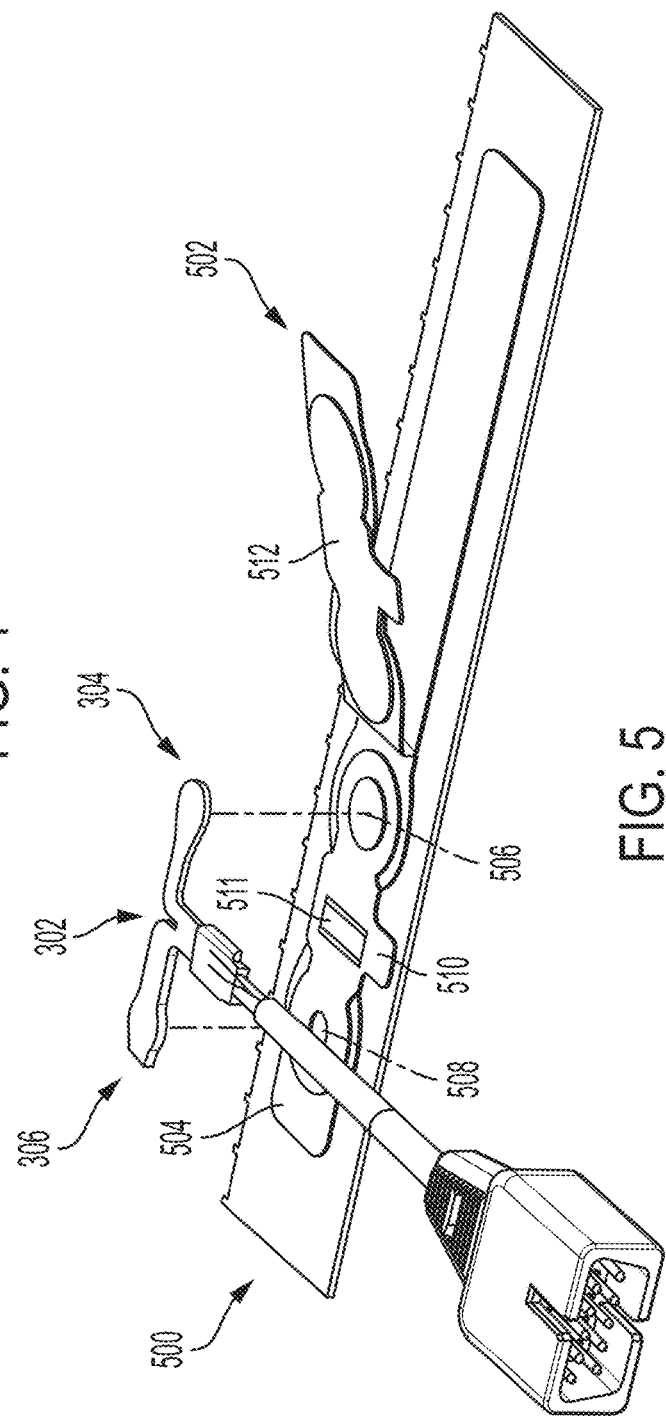
FIG. 5 illustrates a perspective view of an exemplary sensor assembly.

FIG. 5 illustrates a perspective view of exemplary assembly of the flex circuit body 302 positioned between multiple layers (shown generally at 502 and 504) of a bandage 500. LED (at 304) and detector (at 306) are positioned over holes 506 and 508, which provide pathways for light transmission. In exemplary embodiments utilizing an optically absorptive material includes a flat black material as an electromagnetic shielding film on a flex circuit at least partially between an LED and photodetector of the sensor (e.g., on the photodetector lines of a flex circuit, or in any position between an LED and photodetector), as in FIG. 3, assembly of the body 302 with the bandage places the film face down (facing patient-side bandage portion 504) to block light shunting.

Further, optically absorptive materials may be provided at any other position on the flex circuit, or within the bandage. For example, such optically absorptive material may also be provided at least partially on the non-patient side portion of the flex circuit to prevent light shunting near the photodetector.

Further, optically absorptive materials may be provided within the bandage itself, for example as layers 510 (patient side) and/or 512 (non-patient side), or generally otherwise in patient side layer 504 and/or non-patient side layer 502. For example, black pigment or dye may be provided as an addition to or as part of a film or carrier of an adhesive (an example of a black adhesive is Arcare 90366). In exemplary aspects, the optically absorptive material includes a flat black material integrated into the sensor bandage at least partially between the LED and photodetector, e.g., in such a way that it at wraps the optical components of the sensor (to lesser or greater degrees). In further exemplary embodiments, an additional or alternative optically absorptive film (of smaller or larger sizes and thicknesses) may be provided in region 511, between emitter(s) and detector(s), with or without adhesive (as layer 510 may include its own adhesive)

Exemplary materials for bandage, backing or other material includes plastics, such as polypropylene (PP), polyester (PES), polyethylene (PE), urethanes, silicone, or the like. Additionally, various layers of the device may be constructed of one or more hydrophobic materials. Bandage, backing and additional possible layers may comprise a variety of thicknesses and may further incorporate optically absorptive materials therein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A patient monitoring sensor, comprising:
a communication interface, through which the patient monitoring sensor can communicate with a monitor;
a light-emitting diode (LED) communicatively coupled to the communication interface;
a detector communicatively coupled to the communication interface and capable of detecting light;
at least one detector terminal that connects to the detector via photodetector lines of a flex circuit;
at least one LED terminal that connects to the LED via LED lines of the flex circuit;
an optically absorptive material provided at least partially between the LED and the detector to reduce or prevent shunting of the light to the detector, wherein the optically absorptive material comprises a first electromagnetic shielding film portion provided at least partially over the photodetector lines of the flex circuit;
a second electromagnetic shielding film portion provided on a first flap that folds over the at least one detector terminal; and
a third electromagnetic shielding film portion provided on a second flap that folds relative to the first flap, wherein the at least one LED terminal is positioned on the second flap in an unfolded configuration.

2. The patient monitoring sensor of claim 1, wherein the optically absorptive material comprises an optically absorptive black material.

3. The patient monitoring sensor of claim 2, wherein the optically absorptive black material is a flat black absorptive material.

4. The patient monitoring sensor of claim 1, wherein the first electromagnetic shielding film portion is provided on the flex circuit between the LED and the detector.

5. The patient monitoring sensor of claim 1, wherein the first electromagnetic shielding film portion is provided over a majority of the photodetector lines of the flex circuit.

6. The patient monitoring sensor of claim 5, wherein the first electromagnetic shielding film portion is provided over more than 90 percent of the photodetector lines of the flex circuit.

7. The patient monitoring sensor of claim 1, wherein the optically absorptive material is provided as part of a bandage provided over the LED and the detector.

8. The patient monitoring sensor of claim 1, wherein the first flap folds onto a first side of a body of the patient monitoring sensor to fold over the at least one detector terminal, and wherein the second flap folds onto a second side of the body.

9. The patient monitoring sensor of claim 1, wherein the at least one detector terminal and the at least one LED terminal are exposed on a first side of a body of the patient monitoring sensor while the first flap and the second flap are in the unfolded configuration.

10. The patient monitoring sensor of claim 1, comprising a ground connector terminal that connects to a ground connector conductive path, wherein the first electromagnetic shielding film portion is provided at least partially over the LED lines of the flex circuit, at least partially over the ground connector conductive path, or both.

11. The patient monitoring sensor of claim 1, wherein a thickness of the first electromagnetic shielding film portion is less than 25 micrometers.

12. The patient monitoring sensor of claim 1, wherein the first electromagnetic shielding film portion comprises a metallic deposition layer and an insulation layer.

13. The patient monitoring sensor of claim 1, wherein the first flap is positioned on a first side of a body of the patient monitoring sensor and the second flap is positioned on a second side of the body of the patient monitoring sensor in the unfolded configuration.

14. The patient monitoring sensor of claim 1, comprising the optically absorptive material provided at least partially on a non-patient side of the flex circuit of the patient monitoring sensor.

15. The patient monitoring sensor of claim 1, an adhesive provided on a third flap, wherein the third flap folds over the detector at a hinge portion and is secured to a body of the patient monitoring sensor after the third flap is folded at the hinge portion.

16. A method of making a patient monitoring sensor, comprising:
providing a communication interface, through which the patient monitoring sensor can communicate with a monitor;
coupling a light-emitting diode (LED) communicatively to the communication interface;
coupling a detector capable of detecting light communicatively to the communication interface;
connecting the detector to at least one detector terminal via photodetector lines of a flex circuit;
connecting the LED to at least one LED terminal via LED lines of the flex circuit;
positioning an optically absorptive material at least partially between the LED and the detector to reduce or prevent shunting of the light to the detector, wherein the optically absorptive material comprises a first electromagnetic shielding film portion provided at least partially over the photodetector lines of the flex circuit;
positioning a second electromagnetic shielding film portion on a first flap that folds over the at least one detector terminal; and
positioning a third electromagnetic shielding film portion on a second flap that folds relative to the first flap, wherein the at least one LED terminal is positioned on the second flap in an unfolded configuration.

17. The method of claim 16, wherein the optically absorptive material comprises an optically absorptive black material.

18. The method of claim 17, wherein the optically absorptive black material comprises a layer of material provided between the LED and the detector.

19. The method of claim 16, wherein the first electromagnetic shielding film portion is provided over a majority of the photodetector lines of the flex circuit.

20. The method of claim 19, wherein the first electromagnetic shielding film portion is provided over more than 90 percent of the photodetector lines of the flex circuit and at least partially over wires of the detector.

* * * * *